United States Patent
Pendse et al.

(10) Patent No.: US 7,981,937 B2
(45) Date of Patent: Jul. 19, 2011

(54) STABLE DISPERSION OF DBNPA IN VISCOSIFIED BRINE

(75) Inventors: Vijay Vinayak Pendse, Okemos, MI (US); Harry James Moyle, Williamston, MI (US)

(73) Assignee: Aurora Specialty Chemistries Corp. Aurora, Lansing, MI (US)

( * ) Notice: Subject to any disclaimer, the term of this patent is extended or adjusted under 35 U.S.C. 154(b) by 1028 days.

(21) Appl. No.: 11/651,690

(22) Filed: Jan. 10, 2007

(65) Prior Publication Data

US 2007/0160676 A1    Jul. 12, 2007

Related U.S. Application Data

(60) Provisional application No. 60/758,145, filed on Jan. 11, 2006.

(51) Int. Cl.
*A61K 31/165*    (2006.01)
(52) U.S. Cl. .................. 514/619; 424/489; 514/528
(58) Field of Classification Search ............... 514/619; 424/489
See application file for complete search history.

(56) References Cited

U.S. PATENT DOCUMENTS

| | | | |
|---|---|---|---|
| 4,770,694 A | 9/1988 | Iwasaki et al. | |
| 4,800,082 A | 1/1989 | Karbowski et al. | |
| 5,070,105 A | 12/1991 | Segall et al. | |
| 5,627,135 A * | 5/1997 | Gartner | 504/159 |
| 6,987,083 B2 * | 1/2006 | Phillippi et al. | 507/213 |
| 2006/0003023 A1 * | 1/2006 | Williams | 424/661 |

FOREIGN PATENT DOCUMENTS

| | | | |
|---|---|---|---|
| JP | 11256096 | * | 5/1996 |
| WO | WO 97/34480 | | 3/1996 |
| WO | WO 97/34480 | * | 9/1997 |

OTHER PUBLICATIONS

Database WPI Week 199805 Thomson Scientific Kurita Water Ind Ltd London, Great Britain XP-002501187 & XP-002501188.

* cited by examiner

*Primary Examiner* — Gollamudi Kishore
*Assistant Examiner* — Snigdha Maewall
(74) *Attorney, Agent, or Firm* — Alfred D. Lobo

(57) ABSTRACT

A dispersion of 2,2-dibromo-3-nitrilopropionamide ("DBNPA") particles in a restrictedly viscosified concentrated brine solution effectively negates gelling of the brine solution because the naturally occurring gum used does not exhibits Ellis-Plastic behavior in the concentrated brine at a pH of from about 1 to 4. Because the DBNPA particles are much less soluble in the brine than in water, the particles are held in the stable dispersion. Moreover, a dispersion of DBNPA particles in viscosified brine provides at least the same biocidal effect as a solution of DBNPA, relative to the same concentration of DBNPA in solution in glycol, but also concurrently nullifies the degradation of the DBNPA during storage so that the loss due to hydrolysis of the DBNPA is less than 3% over a period of three months at a temperature in the range from $-5°$ C. to $25°$ C. A process is disclosed for making the dispersion which can be stored at a temperature in the range from about $-5°$ C. to $25°$ C. for up to three months with less than 3% by weight of the DBNPA particles settling out, and with less than 3% degradation of the DBNPA, provided the desired salt solution is made first and the remaining ingredients added thereafter.

7 Claims, No Drawings

STABLE DISPERSION OF DBNPA IN VISCOSIFIED BRINE

CROSS-REFERENCE TO RELATED APPLICATION

This application claims the benefit of the filing date of Provisional Application 60/758,145 filed 11 Jan. 2006.

FIELD OF THE INVENTION

An invention is disclosed which relates to an aqueous saline dispersion of 2,2-dibromo-3-nitrilopropionamide ("DBNPA") particles held in high concentration in a restrictedly viscosified biocidal liquid brine yet stable; and, to a method for preparing the dispersion. By "restrictedly viscosified" is meant that the viscosity of the brine dispersion is held in a narrow range, not sufficient to form a gel, which range is maintained by using a viscosifier, preferably an environmentally friendly, biodegradable viscosifier, unreactive with the DBNPA, the viscosifier being in an amount from about 0.3% to less than 1.0% by weight (wt %) of the dispersion. By "biodegradable" is meant that the viscosifier is capable of being decomposed by natural biological processes. By "viscosifier" is meant a viscosifying gum or inorganic thickener such as a suspension aid, also referred to as a dispersing agent or coupling agent.

Since the solubility of DBNPA is only about 1.7 g in 100 g of deionized water at 25° C., and DBNPA is degraded in water, making a solution of DBNPA in water is not practical. The term "brine" as used herein is accorded its usual dictionary meaning, namely, water saturated with, or, containing a large amount of a salt. The term "brine solution" is used herein specifically to emphasize that the brine is a liquid, not solidified, and the liquid is essentially free of dispersed alkali metal halide crystals or alkaline earth metal halide crystals, separately or together referred to herein, for brevity, as "halide(s)". More specifically, as used hereinafter, "brine" refers to an aqueous solution of at least one alkali metal halide or alkaline earth metal halide, either of which, if present alone, is present in an amount at least 20% of the amount required to form a saturated solution at 25° C. (also 20% saturated, or one-fifth saturated). The brine is referred to as concentrated brine when the halide(s) is present in an amount greater than 50% of the amount required to form a saturated solution at 25° C. (also >50% saturated, or more than one-half saturated).

By "essentially free" is meant that the brine has less than 1% by weight ("wt %") of dispersed halide crystals. The dispersion of DBNPA claimed herein is always a liquid in the temperature range at which it is used to obtain treated water. The dispersion is to be used as a biocide to control growth of bacteria in water, which growth makes the water unusable. Treated water so obtained may be discharged into an agricultural environment.

THE PROBLEM

To avoid using a polyalkylene glycol without sacrificing the biocidal potency of DBNPA in an aqueous process stream. To produce a physically and chemically stable, pourable and readily pumpable liquid, aqueous dispersion of solid DBNPA particles in the range from about 20 to 50 parts by weight of undegraded, that is, substantially unhydrolyzed, DBNPA in 100 parts of dispersion. By "substantially unhydrolyzed" is meant that less than 3% by weight, typically from about 0.01% but less than 3% wt % of the DBNPA is degraded during storage at usual, normal storage temperature. By "pourable" is meant that 100 ml of dispersion in a 250 ml beaker may be poured out of the beaker in less than 1 minute. By "pumpable" is meant that the dispersion may be pumped at 25° C. with a conventional rotary gear pump such as a stainless steel Viking® H 724, 1.27 cm (0.5") or, a Liquiflow® 35FS6133U00, without cavitating the pump; or, if a pump is available which was used to pump gel, such as an air powered double diaphragm pump (e.g. a Sandpiper S15, non metallic design level 2 ball valve, inlet/outlet: 3.81 cm (1.5 ins), manufactured by Warren Rupp, USA), it may also be used.

DBNPA, in contact with water, degrades during storage, because the DBNPA hydrolyzes (see "Rates and Products of Decomposition of 2,2-dibromo-3-nitrilo-propionamide", Exner et al., *J. Agr. Food Chem.*, Vol. 21, No. 5, pp. 838-842). Moreover, upon addition of a viscosifier such as xanthan gum to an aqueous DBNPA dispersion, the viscosifier loses a significant portion, typically greater than about 20% or more, of its viscosifying functionality within an acidic composition in about seven days at a pH of about 2.2 or less (see Publication No. US 2002/0147235 to Carlson et al, col 1, 9 lines from bottom).

Nevertheless, a desirable, chemically stable, pourable and pumpable aqueous dispersion is required to exhibit substantially no degradation due to hydrolysis prior to being diluted in use, that is, from about 0.01% but less than 3% wt % of the DBNPA is degraded despite being stored at a temperature in the range from about minus 5° C. (−5° C.) to 35° C. for a chosen period during which the dispersion is to be used if it is to be optimally effective. The period may be as little as 3 weeks and as long as 3 months. Further, the dispersion in brine is required to exhibit substantially no settling, that is, less than 3 wt % of the solid DBNPA settles in a closed container with a gas-tight closure, stored under the aforesaid conditions.

The amount of DBNPA to be added to process water being treated is such that the concentration of DBNPA in the water will kill enough bacteria to negate slime formation, preferably to lower the count to less than $10^6$ per ml of water, and then to degrade rapidly after 24 hr, preferably being substantially completely hydrolyzed after 14 hr from the time of addition. "Process water" to be treated refers to any aqueous stream which is contaminated with microbes enough of which are to be killed so as to leave less than are prone to generate a slime in streams such as the recycle stream in a paper mill or in cooling tower water.

BACKGROUND OF THE INVENTION

The composition of this invention is referred to as a "dispersion" and not a "suspension" because solid particles, typically crystals of DBNPA (which is not a salt), in this dispersed phase, are substantially homogeneously distributed in a continuous phase of brine to yield a stable dispersion, when held as such, in an air-tight closed container without shaking, for a relatively short period, typically no more than three (3) months. By "substantially homogeneously distributed" is meant that there is less than a 10% difference in concentration of DBNPA particles in a layer in the uppermost 10% of the height of the dispersion in a 500 ml graduated cylinder, and a layer in the lowest 10% of the graduate stored in a closed container at 25° C. In a suspension, particularly one in the form of a gel, the DBNPA particles will remain homogeneously dispersed, if not indefinitely, for a very much longer period than they will in a dispersion.

DBNPA, also referred to as 2-cyano-2,2-dibromoacetamide, is a particular haloacetamide widely used as a biocide to control the accumulation of bacterial slime in aqueous systems. Slimes are generated due to the growth of bacteria and/or fungi in aqueous systems including process water used in paper mills, cooling water towers, and various equipment used in unit operations; and, in aqueous systems for the production of cutting oils, textile oils, and water-based paints, inter alia. DBNPA in a low concentration in the range from 10 ppm (parts per million) to 1000 ppm in process water, is found to eliminate putrefaction and contamination which occurs due to the growth of bacteria and fungi. Though rapid degradation of the DBNPA in an aqueous stream, in the range of from 1-hr-12 hr, is a desirable environmental attribute after the DBNPA has functioned as a biocide, such desirable degradation also results in accelerated degradation during storage of the dispersion prior to its use.

To deliver a precise dosage amount of the DBNPA into such aqueous systems, a user would like to dilute a pourable and pumpable aqueous liquid concentrate without any problems associated with dispensing the biocidal concentrate; and, which concentrate when stored generates no undesirable byproducts; and when used has no undesirable effect on the environment. Lastly, a user would like to purchase the desired DBNPA active ingredient without paying for anything which the user does not, or cannot use, or, from which the user cannot benefit in some way.

At present, DBNPA is sold as a stable liquid in a non-aqueous solvent such as a polyalkylene glycol to avoid the hydrolysis problem with free water. Instead of the glycol providing the user with a benefit, the glycol provides nutrition for the bacteria the DBNPA is being used to kill and introduces a small but highly undesirable amount of volatiles. For example, Pluriol® E 200 LS and Pluracol® E 200 LS polyethylene glycol (PEG) from BASF Corp. introduces <1% volatiles. To cut the costs incident to using DBNPA in glycol solvent, Segall et al in U.S. Pat. No. 5,070,105 disclosed one could add some water provided one used various stabilizers. Though degradation is decreased, the cost of glycol, coupled with the cost of removing glycol (not ingested by the microbes) from water discharged into the environment, is still high. This high cost stemming from the high chemical oxygen demand (COD) of the glycol present, makes such non-aqueous, organic solvent formulations undesirable.

Like the solution in glycol, any stable aqueous dispersion is also to be diluted with water to make the biocidal solution. By "stable" is meant both physically and chemically stable. By "physically stable" is meant that less than 3%, typically from about 0.01% but less than 3%, of the solid particles of the DBNPA settle out after being stored in a closed container at a temperature in the range from about −5° C. (minus 5° C.) to 35° C. for a specified period, up to 3 months, during which the dispersion will be used. By "chemically stable" is meant that from about 0.01% to less than 3 wt % of DBNPA is lost due to hydrolysis during the same specified period, up to 3 months, at the same temperature. An "environmentally friendly" viscosifier refers to one which has minimal adverse impact on the natural environment such as is obtained with naturally occurring materials, or man-made materials which behave like naturally occurring materials.

Either a mass of DBNPA solid particles, or a compact or tablet made with the solid particles, is difficult to use, therefore undesirable, as is an aqueous gel requiring fluidization before it can be pumped.

In his U.S. Pat. No. 5,627,135 ("'135 patent" for brevity), Gartner stated that "It would be desirable to discover liquid formulations of DBNPA that utilize water as a suspending medium and in which the DBNPA is protected to prevent or reduce the decomposition or degradation thereof" (see '135, col 2, lines 12-15). He recognized that this type of formulation would (i) not only reduce the COD as compared to the present commercial formulations which employ polyalkylene glycols, but such a formulation would also be less expensive; (ii) that it would be advantageous if a wide range of concentrations of DBNPA could be employed in the formulations; and, (iii) that it would be desirable if the "formulations were insensitive to changes in temperature and electrolyte concentration" (see '135, col 2, lines 22-23). Note that Gartner referring to an electrolyte, states that "The formulations are substantially insensitive to changes in temperature from about 0° C. to about 100° C. and to changes in the electrolyte concentration." (see '135, col 2, lines 36-38), but does not state what the electrolyte is, what its function is, or how much of it is used to do whatever it is supposed to do.

Gartner's solution to the problem was an antimicrobial formulation in water, which formulation comprises from at least about 3 to 70 weight percent ("wt %") DBNPA suspended in at least about 30 to 97 wt % water in the presence of a suspending amount of a thixotrope that exhibits Ellis-Plastic behavior at a pH of from about 1 to about 4. In addition to DBNPA being suspended in a thixotrope, he specifically requires that the thixotrope exhibit the specified Ellis-Plastic behavior. Thus his "liquid formulation" was not a "liquid" until the gel was subjected to enough stress to fluidize it into a liquid state.

That Gartner relies on forming a gel, which exhibits Ellis-Plastic behavior at a pH in the range of from 1 to 4, to negate the hydrolysis is evidenced by his statement that:

"These thioxotropes typically exhibit a yield value which exceeds the force of gravity acting on the DBNPA particles thereby allowing the DBNPA particles to be suspended in water and thus protected from the degrading effects water usually has upon DBNPA." (see '135, col 3, lines 55-60).

Thereafter, with respect to "A series of mixtures ranging from 0.1 to 2 weight percent thixotrope in water", (see '135, col 4, lines 3-5) he states: "Typically, a few minutes of agitation is sufficient to achieve a uniform suspended mixture in the form of a gel for each formulation. However, three hours should pass before Step 2 is undertaken in order that the formulation reaches an equilibrium at which it will exhibit its final thixotropic properties.

2. After three hours have passed, the formulations can now be tested for suitability hi the invention. Gentle agitation is applied to the formulations. If little or no flow occurs upon agitation of the formulation then the thixotrope is not suitable for use in the invention. Suitable thixotropes (assuming they exhibit suitable yield value and stability as determined in step three below) should cause the formulation to liquefy and flow upon agitation and return to its gel form almost immediately upon cessation of agitation." (see '135, col 4, lines 8-22).

With respect to such a thixotrope, he defines "thixotrope exhibiting Ellis-Plastic behavior" as referring "to compounds or mixtures of compounds which cause a formulation to exhibit the following properties. First, the formulation must form a gel which liquefies when agitated, yet returns to the gel state when it is at rest. Second, in contrast to most liquids which will flow when subjected to any shear stress, i.e., force applied to the liquid, no matter how small the stress, formulations of this invention require some minimum amount of shear stress in order to liquefy the formulation and cause it to flow. This minimum amount of shear stress is called the "yield value" and it varies as the particular thixotrope and its concentration vary. The yield value of the thixotrope must be high enough to suspend DBNPA particles in water. This means the yield value must exceed the force of gravity acting on the DBNPA particles or the DBNPA will settle to the bottom." (see '135, col 2, lines 58 to col 3, line 6).

Note that in his Table II, Gartner shows he made two aqueous suspensions, Examples I and II, each having about 50% DBNPA; 0.75% xanthan gum; 0.25% locust bean gum; and 49% water. One (Example II) of the suspensions was aged for 15 months before both were tested for antimicrobial activity; the other was not aged. There is no indication as to whether (I) and (II) exhibited Ellis-Plastic behavior at any pH. Tables IV and V show that (I) and (II) are comparably effective. But there is no indication as to how much of the DBNPA in (II) settled, nor how much had been lost to hydrolysis.

Gartner states "A series of mixtures ranging from 0.1 weight percent to 2 weight percent thixotrope in water are thus prepared. To each of these mixtures, a predetermined amount of solid DBNPA is then added with agitation to prepare a series of formulations containing from 3 to 70 weight Percent DBNPA. Typically, a few minutes of agitation is sufficient to achieve a uniform suspended mixture in the form of a gel for each formulation. However, three hours should pass before Step 2 is undertaken in order that the formulation reaches an equilibrium at which it will exhibit its final thixotropic properties."

Surprisingly, the same or equivalent gum(s), namely, xanthan and locust bean gums which met the requirements (in the '135 patent) to function as a thixotrope, alone or in combination, which exhibits Ellis-Plastic behavior in the '135 patent, when used in an amount totaling less than 1.0 wt % in a dispersion specified herein, fails to form a thixotrope which exhibits Ellis-Plastic behavior. Nevertheless, Gartner states "Generally, the suspending amount is at least about 0.03 weight percent of the total suspension, preferably at least about 0.8, to at most about 4, preferably to at most about 2 weight percent of the total suspension." (see '135, col 4, lines 57-63).

Assuming, if for no logical reason, one considered using a liquid brine in lieu of water, one would expect that, the solubility of DBNPA in brine being even lower than that in water, the tendency of solid DBNPA particles, which have a true density of about 2.35 g/cc, to settle out of the brine dispersion would be much greater than the tendency to settle out of water or brine. In addition, since the pH of the brine before addition of the DBNPA, would be above 4, typically in the range from above 4 but no higher than 6, one would expect that the novel aqueous dispersion in brine would be susceptible to hydrolysis (as stated by Gartner and Carlson).

To avoid the hydrolysis problem in DBNPA, Iwasaki et al in U.S. Pat. No. 4,770,694 teach a biocidal suspension consisting essentially of (a) from 10 to 60 wt % of DBNPA, and (b) from 0.2 to 20 wt % of a phosphate ester salt of a non-ionic surfactant solid as the essential ingredient, thickened with a polysaccharide or gum, e.g. 0.5 part of xanthan gum or guar gum, the latter being well-known thickening agents in aqueous systems. They indicate that their aqueous suspension solves all problems when a specific surfactant is used as the dispersant, and has long shelf life and suspension stability upon dilution (see '694, col 1, lines 52-57). In '694, col 4, lines 25-38, they generically set forth the ingredients to make an aqueous biocide suspension composition having good shelf life and excellent flowability—but they do not state what "good shelf life" means, nor how much the biocide settles. The statement relating to "suspension stability upon dilution" is to be weighed in light of data in U.S. Pat. No. 4,800,082 Karbowski et al, and their statement that "The half-life of DBNPA in this tower was determined to be very short, estimated at less than one hour." (see '082, col 10, lines 32-33). The "tower" referred to is a Marley cooling water tower.

Reverting to the '082 patent to Karbowski et al, they teach making a solid compact of plasticized water-insoluble cellulose ether particles, e.g. methylcellulose, into which DBNPA is reversibly diffused, the compact to be used without a pump, an eductor or a similar dispersing apparatus (see '082, col 2, lines 28-31). Though they disclose a compact of (a) about 1 to 90 percent by weight of a halogenated amide antimicrobial compound, and (b) about 10 to 80 percent by weight of a suitable hydrophilic polymer selected from the group consisting of a natural water soluble cellulosic polymer, a synthetic water soluble cellulosic polymer, gelatin, maltodextrin, xanthan gum, carrageenan, carboxymethyl guar, hydroxypropyl guar and carboxymethyl galactomannose, they do not suggest that the compact is dispersible in water. Nor do they suggest that they could essentially negate degradation by hydrolysis if they used a viscosified brine in which to form a stable dispersion with less than 1 wt % of a hydrophilic polymer such as a gum.

Instead, Karbowski et al suggest placing their solid composition in a perforated polyethylene container through which water is flowed, and water gets treated as it flows over a tablet. They limit the flow of water over the surface of their composition which allows for an even longer treating time period (i.e., prolonged sustained release).

Though they recognized the problem of degradation of DBNPA (see '082, col 1, lines 19-27) they never suggested they could disperse the solid particles of DBNPA in a viscosified brine and provide either a chemically or physically stable dispersion. Repeating one of their examples provides evidence that their dispersion is neither homogeneously dispersible nor sufficiently physically or chemically stable, as required and defined above.

SUMMARY OF THE INVENTION

A dispersion of 20 to 50 parts by wt, preferably from 20 to 40 parts by wt of DBNPA solid particles in 100 parts by wt of a brine composition which has been viscosified with from about 0.3% but less than 1 part by wt of viscosifier, and has a pH in the range from above 4 to about 6 before addition of the DBNPA particles, fails to exhibit Ellis-Plastic behavior at a pH of from about 1 to 4 because the concentration of halides effectively negates gelling of the brine solution. The physical and chemical stability of the dispersion is sensitive both to temperature of storage and of use, and to concentration of the halide(s) in the solution whether the halide is an alkali metal halide or an alkaline earth metal halide, or a combination of both. Since the true density of DBNPA particles is 2.35 g/cc, the higher the density of the brine, the better for long term physical and chemical stability before the dispersion is diluted for use.

The effect of the same concentration (ppm) of DBNPA is surprisingly greater when it is not dissolved in an organic solvent such as PEG but dispersed in brine, such effect being attributable to the effect of the combination of viscosifier and water-soluble halide in the brine. Using DBNPA by dissolving it decreases its effectiveness compared with its effectiveness when it is dispersed.

Use of the dispersion as a biocide avoids environmental concerns such as an increased chemical oxygen demand of industrial waste water, e.g., cooling tower effluent, as set forth in the '135 patent to Gartner.

As long as the brine contains at least 20% by wt of the amount required to saturate the brine solution, using at least one of the aforementioned halides and from 0.3 but less than 1 part of a viscosifier in 100 parts of dispersion, degradation of DBNPA due to hydrolysis is decelerated and reduced. Such degradation is progressively further reduced when the brine contains at least one of these halides in an amount ranging from 20% to 100% of the amount required to form a saturated aqueous solution at 25° C. depending upon which halide or combination of halides is used, and how long the dispersion is to be stored before it is to be used. Most preferred is a combination of a major portion by wt of NaBr and a minor portion of NaCl as this combination provides a solution of desirable density, is readily soluble in process water without contributing to its hardness as would halides of barium or calcium.

To provide physical and chemical stability of a 20% DBNPA dispersion viscosified with 0.3% of viscosifier, over a minimum of 3 weeks, because it is specified that the dispersion is to be used within that time, the brine contains at least 20% of the amount of halide required to form a saturated solution at 25° C., preferably with from 0.05% to 2.% by wt of a suspension aid. Higher concentrations of DBNPA are prepared with a hydrophilic gum present in an amount in the range from 0.1% to 0.7% by wt, optionally in combination with the aforesaid suspension aid.

A preferred brine contains a combination of halide(s) present in the range from 40-80 parts/100 parts process water, and at least one is present in an amount greater than 20%, preferably greater than 30%, of the amount required to saturate the solution at 25° C. (77° F.). To make a suitable brine for this dispersion, one or more halides are selected from the group consisting of an alkali metal halide, an alkaline earth metal halide, and a combination of one with another.

The result is a physically and chemically stable viscosified dispersion which is stable, pourable and pumpable at a temperature in the range from about minus 5° C. (−5° C.) to 35° C. During storage, the stable dispersion exhibits substantially no unacceptable degradation due to hydrolysis. When a 20% DBNPA dispersion is stored in a closed container for 3 weeks at a temperature in the range from about −5° C. to 35° C., prior to being diluted in a process water stream, from about 0.01% to less than 3% by wt of the DBNPA in the dispersion is hydrolyzed. When stored in a closed container for 3 months, at a temperature in the range from about −5° C. to 25° C., from about 0.01% to less than 3% by wt of DBNPA in the dispersion settles as solid particles, and from about 0.01% to less than 3% by wt of the DBNPA in the dispersion is hydrolyzed. The higher the concentration of DBNPA in the dispersion, the higher the concentration of viscosifier required to keep the dispersion stable.

The brine typically has a pH in the range from above 4-6 prior to addition of the DBNPA. A typical dispersion which has from about 10-35 parts of halide(s) and from 20-50 parts DBNPA in 100 parts of the composition has a pH in the range from about 2.5 but no higher than 5, and a viscosity in the range from about 340 cP (Brookfield #2 spindle, 30 rpm) to 30,000 cP (Brookfield #4 spindle, 6 rpm).

A viscosifier refers to a preferably environmentally friendly, biodegradable material, inert with respect to DBNPA, which material increases the viscosity and helps suspend DBNPA particles without forming a gel. The viscosifier may be water-insoluble, as are certain hydrophilic clays and fumed silica or alumina, polyamine amides, polyamides, unsaturated carboxylic acids and the like; or water-soluble, as are various hydrophilic polymers, e.g. polysaccharides. The term "viscosifying gum" is used to identify preferred water-soluble, biodegradable gums, preferably naturally occurring gums in wide use to viscosify an aqueous medium. If used in combination with a suspension aid, at least 0.1% of viscosifying gum is used. Without a suspension aid, from about 0.3=0.8% by wt, most preferably from about 0.4 to 0.6% by wt of the viscosifying gum is used.

As defined, "brine" is formed with one or more halides dissolved in it, in an amount at least 20% by weight of the amount required to saturate deionized water with the halide(s) at 25° C.; preferably an amount at least 50% by weight of the amount required to saturate deionized water is used. For example, a saturated solution of NaBr at 50° C. is 116 g NaBr/100 g of water (see Handbook of Chemistry and Physics, CRC Press); and about 114 g NaBr/100 g of water at 25° C. An aqueous solution containing 22.8 g NaBr/100 g of water is 20% saturated at 25° C. A brine of NaBr is one which contains at least 22.8 g NaBr/100 g water at 25° C., preferably more than 35 g/100 g water. A saturated solution of NaCl is 35.7 g NaCl/100 g of water at 0° C., and 39.12 g NaCl/100 g of water at 100° C. (see, id); and about 36.5 g NaCl/100 g of water at 25° C. An aqueous solution containing 7.3 g NaCl/100 g water is 20% saturated at 25° C. A brine of NaCl is one which contains at least 7.3 g at 25° C., preferably more than 20 g/100 g of water at 25° C. A brine having 40 parts NaBr and 20 parts NaCl in 100 parts by weight of water contains salts in a NaBr concentration $40/114=35.08\%$ of saturated at 25° C.; and, a NaCl concentration $20/36.5=54.8\%$ of saturated at 25° C.

A preferred restrictedly viscosified DBNPA dispersion is one which consists essentially of from about 20-40% by wt of DBNPA and halide(s) which is/are present in the range from about 20-30% by wt. Preferably at least 10 parts of NaBr is always present along with from 0.1 to less than 1 part, preferably from about 0.4-to 0.7 part by wt of one or more gums, in 100 parts by wt of the dispersion.

When plural halides are used, though the brine may contain much less than the amount of either halide required, by itself, to saturate the solution, the brine is preferably "essentially saturated", that is, it has more than 75%, preferably more than 90% of the amount required to saturate the solution at 25° C. For example, a brine using a combination of halides such as NaBr and NaCl has at least 40 parts, preferably from 50-75 parts of these halides in 100 parts of water. The amount(s) required to essentially saturate the brine at a chosen temperature will vary depending upon the combination of halides used. In the most preferred dispersion, the water is so saturated with halide(s) that addition of as little as 10% more of one of the halides to the dispersion will result in more than 3% by wt of halide settling out after being stored at 25° C. for the specified period during which the dispersion is to be used, up to three months. Though such settling is not harmful, it is visually, cosmetically undesirable.

The physically and chemically stable combination of DBNPA, viscosifier and brine is diluted to provide an effective amount in an aqueous stream to be treated. By "effective amount" is meant a concentration of DBNPA (in the stream) that provides the desired degree of microbial control, typically a count of less than 6 million on a Petrifilm® agar plate (available from 3M Company) in 14 hr or less after addition of the dispersion to process water.

A process is disclosed for maintaining a restrictedly viscosified dispersion of DBNPA particles in a brine, preferably concentrated brine, medium which dispersion, being a liquid, seeks its own level in a closed container at 25° C.; and, the dispersion can be stored at a temperature in the range from about −5° C. to 25° C. for up to three months with less than 3% by weight of the DBNPA particles settling out, and with less than 3% degradation of the DBNPA. Such criteria adequately meet or exceed the requirements of a stable biocidal composition.

A stable biocidal composition consists essentially of a dispersion of DBNPA particles in the size range from about 45 nm (325 mesh Standard Test Sieves—Wire Cloth) to 175 µm (100 mesh), substantially homogeneously distributed throughout a brine solution viscosified with from about 0.3 to 0.8, preferably from 0.4 to 0.6 parts by weight of at least one viscosifier, and if more than one, each preferably biodegradable, then the combined weight of the viscosifiers is in the stated range per 100 parts by weight of the dispersion. The brine solution is at least 20% saturated with a water-soluble alkali metal halide or alkaline earth metal halide, or both. By "20% saturated" is meant that the halide(s) is/are present in an amount at least 20% by wt, preferably more than 30% by wt, of the amount required to saturate deionized (or distilled) water at 25° C. Most preferably, water used to make the dispersion is first saturated with the less soluble halide, and the more soluble halide added later.

The foregoing dispersion is typically used to control unwanted microbial growth, such as biological slime, which tends to accumulate in process equipment for aqueous streams, including water treatment systems and other equipment through which an aqueous stream flows, by adding a small amount of the dispersion, the small amount calculated to provide the desired concentration in a particular aqueous stream.

DETAILED DESCRIPTION OF PREFERRED EMBODIMENTS

Substantially pure DBNPA is currently commercially available as a finely divided solid, with most particles ($\geqq$95%) in the relatively large size range of from 150 µM (80 mesh Standard Test Sieves—Wire Cloth) to 175 µm (100 mesh). Crystalline DBNPA is preferred for ease of dispersing and suspending it in the water. These relatively large particles makes it more difficult to keep them stably dispersed for several months than if they were smaller. To get even less settling than stated above in the same 3-month storage period it may be desirable to use particles, a large portion, at least 25% of which, are as small as 5 µm to 45 µm (325 mesh), the remaining being in the size range up to 175 µm. However, particles in a stable dispersion having more than 50% of them in the range 5-45 µm, tend to hydrolyze more easily during storage, and the rate of hydrolysis increases as pH increases above 7. On balance, it is preferred to use particles in the larger size range which are physically stable for 3 months at up to 25° C. and chemically stable, as defined above, for much longer.

With respect to the insensitivity to electrolyte, Gartner offers no evidence to support the statement above (see '135 col 2, lines 36-38). The only examples he provided show using in the range from 0.009 to 0.030 parts by weight of oxalic acid in the range from 49.62 to 48.67 parts of water respectively, indicating a maximum concentration of about 0.06 percent.

The novel dispersion of DBNPA in brine, preferably concentrated, more preferably >90% saturated, is non-buffered; and the halide is present in a concentration of at least 20 wt % of the amount required to saturate water. For NaCl electrolyte (salt), it is present as 7.3 g in 100 g water at 25° C.; and for NaBr, it is present as 22.8 g in 100 g water at 25° C. in 100 parts of water. Thus, at the low end of 7.3/107.3=7% concentration of NaCl in the solution, this concentration is about 100 times greater than the maximum concentration shown in Gartner. This concentration appears to result in the DBNPA in the novel dispersion being essentially free from degradation due to hydrolysis.

The conventional wisdom is that degradation due to hydrolysis increases as the concentration of salt, which is the electrolyte in solution, increases, and as stated in the '135 patent, it is generally desired to employ a formulation which is insensitive to changes in temperature and electrolyte concentration. It is therefore surprising that not only is the DBNPA dispersion physically stable in both brine, and also in an essentially saturated brine, but the dispersion is also chemically stable in storage. It is not critical that the DBNPA dispersion be in an essentially saturated brine, though such is preferred for long storage.

The Brine Solution:

The rates of settling of DBNPA particles at 25° C. in the following brines are compared to the rate of settling in distilled water:
(a) saturated NaCl solution;
(b) 40% saturated NaBr solution (40% of amount required to saturate);
(c) 20% saturated NaCl solution (20% of amount required to saturate);
(d) 20% saturated NaBr solution (20% of amount required to saturate);
(e) 20% saturated NaCl solution and 20% saturated NaBr solution in equal amounts;
(f) distilled water.

Soon after thoroughly mixing the DBNPA in each dispersion, 250 ml of each dispersion is placed in a 250 ml straight-walled jar. In each case, complete separation of the DBNPA particles occurs in less than 30 seconds, the rate of separation from (b) being only slightly slower than that of the other dispersions, which rates of other dispersions are substantially the same as that from (f), the distilled water.

Since the specific gravity of the brine is typically in the range from 1 to 1.3 which is about half of that of the DBNPA particles, it is evident that the unviscosified brine does not contribute substantially to keeping the DBNPA particles in suspension. On the other hand, the high concentration of halide in the brine, and the resulting high concentration of metal ions and halogen ions, would be expected to accelerate the precipitation of DBNPA particles from the brine. Unexpectedly, the higher the concentration of halide(s) the better the physical and chemical stability of the dispersion.

If only NaCl is used to saturate the brine, it contains about 36.5 parts of NaCl per 100 parts of deionized water at 25° C. When such a viscosified saturated NaCl solution is stored for 3 months at 25° C., less than 3% of the DBNPA and less than 3% by wt of the NaCl settles out of the dispersion. Typically less than 1% by wt of DBNPA settles, and such small amount of NaCl as may settle is not harmful but is nevertheless undesirable because the precipitated NaCl may be mistaken for precipitated DBNPA.

Less halide may be used if the dispersion is not to be stored for more than 3 weeks. If a single halide is used, the amount used is at least 20% of the amount required to form a saturated solution at 25° C. the amount used in a particular dispersion being chosen depending upon the particular halide and the mount of viscosifier used.

When a combination of halides, e.g. NaBr and NaCl, is used, the brine is preferably saturated with respect to at least one halide, typically NaCl. If the stable dispersion is in a solution which is supersaturated with respect to at least one halide, from about 0.01% to less than 3% by wt of the supersaturating halide may precipitate from the solution, and this is not harmful, though visually, cosmetically undesirable. Therefore, the concentration of the halides in a stable brine solution in which DBNPA particles are dispersed, is such that the brine is not so saturated that 3 wt % or more of the halide is precipitated from the brine when stored for 3 months at 25° C. Typically, in a brine dispersion containing (i) 40 parts DBNPA, (ii) a major amount by weight JO NaBr, e.g. from 10-30 parts, and (iii) from 5-15 parts of NaCl, in 100 parts by wt of dispersion, the NaCl being present in a minor amount relative to the NaBr, the brine is essentially saturated relative to the NaCl.

Preferably the brine is a solution of two halides, one in a major proportion by weight relative to the other, each in an amount at least 20 wt % of the amount required to form a saturated solution at 25° C. Most preferably, the salt present in a major amount is sodium bromide (that is, >50 parts of NaBr relative to 100 parts combined salts). The salt present in a minor proportion by weight (that is, <50 parts of minor salt relative to 100 parts combined salts), is preferably selected from sodium chloride and calcium chloride. In the best mode the salts are together present in amounts in the range from 10 to 25 parts NaBr, and from 5 to 15 parts NaCl or $CaCl_2$.

The Viscosifier:

By viscosifying the dispersion of DBNPA in a concentrated brine solution with a small amount of viscosifier insufficient to cause gelling at 25° C., but sufficient to maintain a viscosity in the above-stated range, the dispersion remains an aqueous, substantially non-acidic liquid brine in which the DBNPA is shielded against hydrolyisis at any temperature in the range from about −10° C. to 35° C.

The viscosifier is preferably selected from a naturally occurring inorganic thickener such as bentonite or attapulgite clay; a hydrophilic polymer unreactive with DBNPA and a halide salt in aqueous solution; and water-soluble polysaccharides or glycans both linear and branched, and their derivatives; each used in a small amount, so that, if more than one is used, their combined amount is in a narrow range, typically from about 0.3 wt % to about 0.75 wt %, insufficient to gel the dispersion, but sufficient to provide the desired viscosity. Preferred are naturally occurring gums which are plant and microbial polysaccharides, or their derivatives, particularly those which can be readily dispersed in either cold or hot water to produce viscous solutions [see *Encyclopedia of Polymer Science and Technology*, by R. L. Whistler, Vol. 11, page 403 (1969)]. Most preferred are biodegradable, naturally occurring viscosifying gums, arabinogalactans, pectins, starch, modified starch and polysaccharide derivatives.

Examples of natural gums that are widely used industrially are the algal (seaweed) extracts such as carrageenan, the exudate gums such as gum arabic and tragacanth, the seed gums such as guar and locust bean, the microbial polysaccharides such as xanthan, and certain polysaccharide derivatives such as carboxymethyl cellulose (CMC), polydextrose, and carboxymethylguar gum. Although natural gums are widely used particularly in the food industry as thickeners and as suspending agents, gums are expensive relative to starch. Therefore it may be desirable to use a combination of a viscosifying gum and starch. Most preferred is a gum commercially available as Ticaxan® Rapid Powder from TIC Gums Corp., used in an amount in the range from about 0.4% to 0.6% by weight of the dispersion.

The following data provide relevant physical properties of viscosified brine solutions:

The progressive change in viscosity as a function of concentration of the natural gum viscosifier in a brine solution having a pH of about 7, is set forth in the following Table I. The solution is made by supersaturating deionized water at 40° C. and pouring off the supernatant liquid after allowing the hot solution to cool to 25° C. The particular natural gum used is prehydrated Ticaxan® Rapid Powder believed to be processed xanthan gum.

TABLE I

| % Prehydrated Gum in Brine (saturated solution of NaCl) | Viscosity (cp) @ 25° C. |
|---|---|
| 0.2 | 105 (#2 spindle, 30 rpm) |
| 0.3 | 340 (#2 spindle, 30 rpm) |
| 0.4 | 650 (#2 spindle, 30 rpm) |
| 0.5 | 5000 (#4 spindle, 6 rpm) |
| 0.6 | 7000 (#4 spindle, 6 rpm) |
| 0.7 | 30000 (#4 spindle, 6 rpm) |

The difference in progressive change in viscosity as a function of concentration of the same prehydrated Ticaxan® Rapid Powder viscosifier in a calcium chloride brine solution is set forth in the following Table II. The calcium chloride brine is also made by supersaturating deionized water at 40° C. and pouring off the supernatant liquid after allowing the hot solution to cool to 25° C. A calcium halide may be used in process water where hardness is not objectionable but is undesirable in treating cooling tower water.

TABLE II

| % Prehydrated Gum in Brine (saturated solution of $CaCl_2$) | Viscosity (cp) @ 25° C. |
|---|---|
| 0.2 | 900 (#2 spindle, 12 rpm) |
|  | 450 (#2 spindle, 30 rpm) |
| 0.3 | 1675 (#2 spindle; 12 rpm) |
|  | 860 (#2 spindle, 30 rpm) |
| 0.4 | 3100 (#2 spindle, 6 rpm) |
|  | 1600 (#2 spindle, 12 rpm) |
| 0.6 | 8500 (#4 spindle, 6 rpm) |
|  | 5000 (#4 spindle, 12 rpm) |
|  | 2400 (#4 spindle, 30 rpm) |
| 0.6 | 14000 (#4 spindle, 6 rpm) |
|  | 7500 (#4 spindle, 12 rpm) |
|  | 3800 (#4 spindle, 30 rpm) |

The viscosity at 0.7% was too high to be measured with a #4 spindle.

It is evident that the viscosity will change appreciably as a function of the amount of viscosifier used.

The specific gravities, measured pH, and viscosities at 25° C. of viscosified distilled water, and of viscosified low concentration brines containing only 20% by wt of the amount of alkali metal halide required to saturate the solution, are presented below:

Table III (a)-III (f)

Table III (a) 0.7% Ticaxan prehydrated gum solution in distilled water only, has a sp. gr. of 1.0 and a pH of 5.8. The viscosity is found to be as follows:

| Spindle # | Rpm | Reading | Viscosity (cp) |
|---|---|---|---|
| 2 | 12 | 52 | 1300 |
| 2 | 30 | 56 | 560 |
| 2 | 60 | 60 | 300 |

Table III (b) 0.8% Ticaxan prehydrated gum solution in distilled water only, has a sp. gr. of 1.0 and pH of 5.8. The viscosity is found to be as follows:

| Spindle # | Rpm | Reading | Viscosity (cp) |
|---|---|---|---|
| 2 | 12 | 55 | 1375 |
| 2 | 30 | 63 | 630 |
| 2 | 60 | 76 | 380 |

The dispersions with this particular gum (Ticaxan) at 0.8% is lumpy and the viscosities read are those of the liquid portion only.

Table III (c) 0.7% Ticaxan prehydrated gum solution in saturated NaCl solution only has a sp. gr. of 1.2 and pH of 5.4. The viscosity is found to be as follows:

| Spindle # | Rpm | Reading | Viscosity (cp) |
|---|---|---|---|
| 3 | 6 | 60 | 12000 |
| 3 | 12 | 66 | 6600 |
| 3 | 30 | 72 | 2880 |

Table III (d) 0.8% Ticaxan prehydrated gum solution in saturated NaCl solution only has a sp. gr. of 1.2 and pH of 5.4. The viscosity is found to be as follows:

| Spindle # | Rpm | Reading | Viscosity (cp) |
|---|---|---|---|
| 3 | 6 | 71 | 14200 |
| 3 | 12 | 79 | 7900 |
| 3 | 30 | 86 | 3440 |

Table III (e) 0.6% Ticaxan prehydrated gum solution in "20%" saturated NaCl solution only has a sp. gr. of 1.08 and pH of 4.8. The NaCl brine is made with 288.4 g distilled water+21.93 g NaCl+1.81 g Ticaxan prehydrated gum. The viscosity is found to be as follows:

| Spindle # | Rpm | Reading | Viscosity (cp) |
|---|---|---|---|
| 3 | 6 | 25 | 5000 |
| 3 | 12 | 30 | 3000 |
| 3 | 30 | 36 | 1440 |
| 3 | 60 | 41 | 820 |

Table III (f) 0.6% Ticaxan prehydrated gum solution in "20%" saturated NaBr solution only has a sp. gr. of 1.23 and pH of 4.8. The NaBr brine is made with 232.5 g distilled water+68.5 g NaBr+1.80 g Ticaxan prehydrated gum. The viscosity is found to be as follows:

| Spindle # | Rpm | Reading | Viscosity (cp) |
|---|---|---|---|
| 3 | 6 | 38 | 7600 |
| 3 | 12 | 40.5 | 4050 |
| 3 | 30 | 48 | 1920 |
| 3 | 60 | 53 | 1060 |

The following data presented in Table IV below, track the physical stability of a dispersion containing 40 parts by weight of DBNPA particles in the above-stated 150-175 μm size range dispersed in 60 parts of a saturated solution of NaCl made as described above and including the stated concentrations of the same prehydrated Ticaxan® Rapid Powder viscosifier. The dispersions were held in 250 ml straight-walled jars at 25° C. The first observations were made 24 hours after the dispersions were made; the second observations, two weeks after the first; the third observations, four weeks after the first; the fifth, five weeks after the first.

TABLE IV

| .Prehydrated Gum (%) | 0.2 | 0.3 | 0.4 | 0.5 | 0.6 | 0.7 | 0.8 |
|---|---|---|---|---|---|---|---|
| One day after prep'n | 50% in liq 50% set'ld | 45% in liq 55% set'ld | ~10% in liq ~90% set'ld | No separ'n observed | No separ'n observed | No separ'n observed | No separ'n observed |
| 2 wks after prep'n | 54% in liq 46% set'ld | 55% in liq 45% set'ld | 45% in liq 55% set'ld | <1% in liq >99% set'ld | No separ'n observed | No separ'n observed | No separ'n observed |
| 3 wks after prep'n | 55% in liq 45% set'ld | 54% in liq 46% set'ld | 46% in liq 54% set'ld | 2.5% in liq 97.5% set'ld | <1% in liq >99% set'ld | No separ'n observed | No separ'n observed |
| 4 wks after prep'n | 54% in liq 46% set'ld | 54% in liq 46% set'ld | 48% in liq 52% set'ld | 3.0% in liq 97% set'ld | 1% in liq 99% set'ld | No separ'n observed | No separ'n observed |
| 5 wks after prep'n | 54% in liq 46% set'ld | 54% in liq 46% set'ld | 48% in liq 52% set'ld | 10% in liq 90% set'ld | 1% in liq 99% set'ld | No separ'n observed | No separ'n observed |

From the above data it is evident that, using the specific Ticaxan gum alone in a concentration of 0.5% in the 40% DBNPA dispersion, it is physically stable after three weeks, showing less than 3% settling of solids.

In an analogous experiment, a concentration of 0.6% in a 20% DBNPA dispersion is physically stable after three weeks at 25° C., with less than 3% settling of solids. A concentration of 20% DBNPA may be kept both physically and chemically stable for up to three months with a combination of from 0.1%-0.4% hydrophilic gum and suspension aid such as fumed silica.

At any concentration from 0.3% to less than 1% of viscosifier in the dispersion, no gel is formed, but the physical stability of the dispersion at a chosen concentration of viscosifier decreases as concentration of DBNPA at the chosen concentration increases.

Though at the maximum concentration of DBNPA, 0.8% Ticaxan provides no settling, homogeneity of the dispersion begins to diminish. It is therefore desirable to use a combination of viscosifers, including combinations of gums and combinations of suspension aids, and of one with the other, to provide better homogeneity.

The physically and chemically stable dispersion disclosed above is found effective as a microbiocide on each of the major genus of microorganisms typically found in aqueous systems. These genus include *Pseudomonas*, Coliforms, *Bacillus Megaterium, Enterococcus* and *Saccharomyces Cerevisiae* which abound in process water, are representative of bacteria which are Gram negative, Gram positive, non-spore-forming, spore-forming and include yeasts.

*Pseudomonas* is a virulent, difficult-to-kill Gram negative, non-sporulating microorganism naturally present in soil and it usually establishes itself as the dominant species in open recirculating cooling systems. *Pseudomonas* is known to metabolize at least 75 different organic chemicals, amongst which one can find phenol derivatives and ethane. Chlorine at a concentration about 0.1 ppm destroys *Pseudomonas* but is not easy to use in industrial aqueous systems.

Coliforms are Gram negative microorganisms found in cooling water ponds. The excellent kill-efficiency of DBNPA is evidenced by a low coliform count. *Bacillus megaterium* is a Gram positive, spore-forming microorganism which are found in cooling water in which nutrition is plentiful. Spores, which form when normal, healthy vegetative cells experience an adverse change in environment, can remain viable with negligible respiratory activity for many years. They are killed only with difficulty by chemicals that destroy vegetative cells on contact, because the walls of spores are impenetrable to most chemicals except chlorine and DBNPA.

*Enterococcus* is a Gram positive, non-spore-forming microorganism, which is not generally found in process water streams, except those in plants for the manufacture of cosmetics.

*Saccharomyces cerevisiae* is a yeast. Yeast, unlike all the previously mentioned bacteria, contains a true nucleus. Fungi are non-photosynthetic eukaryotes ("possessing a true nucleus"), and divide into several sub-groups, one of which are yeasts. Yeasts, unlike other fungi, do not form mycelium, but DBNPA is effective against numerous strains of yeast when used in a range from about 100 ppm to 0.1 percent by weight of aqueous stream.

The following is a comparison of the stability of two dispersions (i) and (ii) in each of which the amount of each ingredient used is given in parts by weight:
(i) the dispersion of this invention consisting of 40 parts DBNPA, 14 parts by wt of NaBr in 40%. NaBr solution and 9 parts NaCl in 25 parts pf saturated NaCl solution, viscosified with 0.6 parts of prehydrated Ticaxan® Rapid gum; and,
(ii) a dispersion in 100 parts of water of a 1 gram tablet prepared as described in '082 to Karbowski et al, composition # 7 of Example I.

Composition # 7 is made as follows: (a) 40 parts DBNPA; (b) 30 parts Methocel K 15M; (c) 27 parts dicalcium phosphate dihydrate; and (d) 3.0 parts stearic acid, are mixed and manually ground in a mortar and pestle until the particles pass an 80 mesh screen. The powder is then dispersed in 100 parts water.

TABLE V

| Dispersion | Physical Stability | Chemical Stability |
| --- | --- | --- |
| (i) | Stable | Stable |
| (ii) | Unstable* | Unstable* |

Unstable*, physically because more than 3% by weight settles after 3 months at 25° C.; and, Unstable*, chemically because more than 3% by weight is hydrolyzed after 3 months at 25° C.

It is noted that in a particular instance, Karbowski et al chose to substitute from 39.5 to 40.5% NaCl for an unidentified antimicrobial compound (see Example IV) to make tablets in which they combined the salt with from 29.5 to 30.3% Methocel K15M; but it is not stated why these tablets without DBNPA were made with varying amounts of different compression agents, e.g. stearic acid, dicalcium phosphate dihydrate, Avicel PH101, etc.

Still further, it is noted that Karbowski et al used DBNPA to treat cooling water in a cooling tower, using slug doses of DBNPA to provide 3 ppm of DBNPA "7 days a week, by metering a 5 percent solution of DBNPA over a 15 minute period." (see col 9, lines 15-17). It is not clear why they used asolution of DBNPA rather than a dispersion of one of the tablets they showed they could make. Suffice it to say that the difficulty of distributing the dispersion through the water in the cooling tower may have dictated the procedure.

Thereafter, Karbowski et al treated the tower (no indication how it was treated) with "timed-release tablets containing DBNPA on two occasions". These were 250 gram tablets containing 40% DBNPA and 30% Methocel K15M. No dispersion of the solid tablet was made.

To Determine Chemical Stability of Dispersions:

The extent to which various dispersions are hydrolyzed is determined by analyzing the amount of DBNPA present in the dispersion (i) at the end of 72 hrs, (ii) at the end of 12 days, and (iii) at the end of 30 days.

To begin with, the purity of the DBNPA powder is analyzed as follows:
i) In a 250 ml Ehrlenmeyer flask, take a known weight (W) of DBNPA powder.
ii) Add 10 ml acetonitrile reagent and swirl.
iii) Add 2 ml of 6N HCl reagent.
iv) Add 20 ml of 10% potassium iodide solution. Cover the flask with aluminum foil and keep in dark place for at least 20 minutes.
v) Titrate the mixture against 0.1 N sodium thiosulfate reagent using starch solution as the indicator. Initial dark blue color becomes colorless at the end point. Record the volume (V) of 0.1 N sodium thiosulfate used.
vi) The % amount of DBNPA present is calculated=V× 0.6045/W Using the foregoing procedure, the DBNPA content of two samples of the DBNPA powder from different portions of the container were found to be 99.8% and 100.2% respectively, indicating there may be an experimental error of up to about 0.5%.

Measurement of Physical and Chemical Stability:

A dispersion of 20% by wt of DBNPA in unviscosified distilled water held in a 250 ml straight-walled jar having a diameter of 3.81 cm (1.5"), shows visible separation of particles at the end of 30 days at 25° C. and degrades up to about 5% at the end of 30 days at 25° C.; it degrades up to about 10% at the end of 30 days at 35° C.

Viscosified dispersions may be prepared with as little as 0.1% of viscosifying gum in combination with a suspension aid to make the dispersion. It is preferred to use at least 0.3% of at least one viscosifying gum in combination with from 0.1-0.5% suspension aid. How long, and the conditions under which a particular concentration of the dispersion is expected to be stored, determines how it is viscosified. The longer the storage period required for a particular concentration, the higher the concentration of viscosifier, or combination of viscosifiers.

Preferred suspension aids are submicron particles, preferably nanometer-size, in the range from 5-50 μm, and include fumed silica or alumina such as Aerosil® R972 and R974, and aluminum oxide C, available from Degussa.

The following viscosified dispersions were prepared, each with a weighed amount of DBNPA which will provide a 20% (±0.5%) DBNPA content in the dispersion.

For example, when 22.9 g of DBNPA is dispersed in 91.1 g of a viscosified NaCl brine containing 20% of the amount of NaCl required to saturate distilled (or deionized) water, a 20.08% dispersion is produced. The viscosified NaCl brine is prepared using 288 g distilled water+21.93 g NaCl+1.81 g Ticaxan gum.

The following dispersions are prepared, each with 20% DBNPA by weight:
(A) 0.7% Ticaxan prehydrated gum soln (solution) in distilled water
(B) 0.7% Ticaxan prehydrated gum soln in saturated NaCl solution at 25° C.
(C) 0.8% Ticaxan prehydrated gum soln in distilled water
(D) 0.8% Ticaxan prehydrated gum soln in saturated NaCl solution at 25° C.
(E) 0.6% Ticaxan prehydrated gum soln in 20% of saturated NaCl soln at 25° C.
(F) 0.6% Ticaxan prehydrated gum soln in 20% of saturated NaBr soln at 25° C.

Upon standing at 25° C. in the 250 ml straight-walled jar (same as used above), none of the foregoing viscosified dispersions showed visible settling of the DBNPA particles (i) at the end of 72 hrs, (ii) at the end of 12 days, and (iii) at the end of 30 days.

Upon standing at 35° C. in the straight-walled jar, none of the dispersions showed visible settling of the DBNPA particles even at the end of 30 days, but dispersions (A), (B), (E) and (F) showed a decrease in DBNPA content of up to about 10% at the higher temperature.

None of the foregoing dispersions showed degradation due to hydrolysis of DBNPA after three weeks and up to 3 months at 25° C.

It is concluded that the low concentrations of gum in the foregoing viscosified solutions have a stabilizing effect upon the DBNPA, as does the presence of the brine.

The following examples 1 and 4 were duplicated from Example I of the Gartner '135 patent.

TABLE VI

Examples from Prior At

| Ex. | Xanthan | Locust bean | Water | Oxalic acid | DBNPA (%) | pH |
|---|---|---|---|---|---|---|
| 1 | 1.000 | 0.335 | 48.67 | 0.030 | 49.97 | 2.4 |
| 2 | 0.772 | 0.259 | 48.94 | 0.023 | 50.01 | 2.4 |
| 3 | 0.516 | 0.173 | 49.45 | 0.015 | 49.85 | 2.4 |
| 4 | 0.305 | 0.102 | 49.62 | 0.009 | 49.96 | 2.4 |

Examples 1, 2 and 3 formed gels after being allowed to stand for 24 hr at 25° C.—the gel liquefies upon being stirred and returns to the gel state when allowed to rest.

Example 4 does not form a gel after being allowed to stand for 24 hr at 25° C.—appreciable settling of DBNPA particles is evident at the end of 24 hr; it forms a gel when stored at 5° C. for 24 hr.

The following illustrative examples illustrate the dispersion of this invention in two formulations (A) and (B):
(A) dispersion with 20 parts by weight DBNPA per 100 parts of dispersion:

|  | parts by wt | parts by wt |  |
|---|---|---|---|
| 40% NaBr soln. | 54.4 | 21.76 | NaBr |
| Saturated-NaCl soln. | 25 | 9.0 | NaCl |
| DBNPA | 20 | 20 | DBNPA |
| Prehydrated Xanthan Gum | 0.6 | 0.6 | |
|  |  | 48.64 | water |
| Concentration of NaBr in water = 21.76/48.64 = 44.49% | | | |
| Concennition of NaCl in water = 9.0/48.64 = 18.5% | | | |

In combination the halides are present in a concentration of 63 parts in 100 parts water.

(B) dispersion with 40 parts by weight DBNPA per 100 parts of dispersion:

|  | parts by wt | parts by wt |  |
|---|---|---|---|
| 40% NaBr soln. | 35. | 14.0 | NaBr |
| Saturated NaC1 soln. | 25 | 9.0 | NaCl |
| DBNPA | 40 | 40 | DBNPA |
| Prehydrated Xanthan Gum | 0.6 | 0.6 | |
|  |  | 36.4 | water |
| Concentration of NaBr in water = 14/36.4 = 38.46% | | | |
| Concentration of NaCl in water = 9.0/36.4 = 24.7% | | | |

In combination the halides are present in a concentration of 63.2 parts in 100 parts water.

Preferred Manner of Making a Dispersion with Mixed NaBr and NaCl:

The required amount of water, sodium chloride and sodium bromide are measured into a large beaker and mixed under low shear mixing conditions until all the salts dissolve completely. Xanthan gum is added to the well agitated (30 to 60 rpm) solution and heated to within the range from 60-70° C. until the gum is uniformly dispersed. The mixture is cooled to room temperature and the chosen amount of DBNPA is added and mixed at moderate speed (10-20 rpm) until the DBNPA is homogeneously dispersed.

Making salt solution first then adding gum and DBNPA is the preferred mode of preparation. Making gum solution first then dissolving salts does not provide a satisfactory dispersion; making the restrictedly viscosified solution first, then adding the halide salt(s) is difficult as the salt(s) do(es) not dissolve even after 24 hrs mixing.

Procedure for Measuring Effectiveness of the DBNPA:

A sample of microbe-laden, odoriferous "white water" from a paper mill is used. "White water" is the term used to identify process water collected from a paper machine after a continuous sheet of paper is formed. Because this water is recirculated for reuse it becomes progressively contaminated with microbes. It is desired to kill as many microbes within as short a period as is economical.

The number of microbes surviving after treatment is counted on nutrient agar "aerobic count" plates made by 3M Company to grow bacterial colonies. Such a plate has upper and lower sheets of plastic, the upper sheet being used to cover the lower sheet. The lower sheet has a grid marked on it, and the grid is covered with a layer of nutrient agar.

Conventionally used sterilized saline solution (8% sodium chloride) supplied by Edge Biologicals, Memphis, Tenn. is used to dilute the treated samples.

Because the process water is so heavily contaminated as to produce a slime, it is diluted, several orders of magnitude, to allow one to count visually the colonies grown on aerobic count plates obtained from 3M Company. Without dilution the number of colonies would be too large to be visually distinguished and counted. Therefore each sample of process water was diluted 10,000 and 1,000,000-fold (times) before 1 ml of the diluted sample was smeared on the gel in an aerobic count plate. Though samples from each dilution were prepared and incubated as described below, only those samples which had few enough colonies to allow an accurate visual count are reported, the others being discarded.

The $10^4$ dilution was made by first making a $10^2$ dilution as follows:

0.1 ml of the process water is measured into a first vial containing 9.9 ml of sterilized saline solution. This gives a dilution factor of 100. Because, upon incubation, 1 ml would give too many colonies to be counted, the $10^2$ dilution was diluted again by adding 0.1 ml of it to a second vial containing 9.9 ml of sterilized saline solution This gives a dilution factor Of $10^4$ and 1 ml of this $10^4$ dilution was spread as a thin film on each of three agar count plates which were incubated in an incubator maintained at 40°±1° C. for 48 hrs. The area, produced by lightly pressing the upper film, corresponds approximately to that of a circle of ~20 cm². Immediately after removal from the incubator, the number of colonies growing on each plate were examined. If the number was small enough that individual colonies could be counted, they were, and the average number recorded.

If the number was too large, 1 ml of the $10^4$ solution was placed on the lower film of each of three aerobic count plates, and spread as a thin film as before. When colonies produced with the $10^4$ dilution were still too many to be counted reliably, 0.1 ml of this dilution was added to a third vial containing 9.9 ml of sterilized saline solution. This gives a dilution factor of $10^6$ (1 MM). 1 ml of this solution was placed on the agar of a count plate and spread as before.

In the following Table VII is presented a comparison of the biocidal effectiveness of several dilutions of DBNPA (i) obtained by diluting a PEG solution of 20% DBNPA in distilled water; and of DBNPA (ii) obtained by diluting a 20% dispersion of DBNPA in viscosified brine (mixture of 21.76 NaBr, 9.0 NaCl, 20 DBNPA, 0.6 Xanthan gum, all in parts by wt).

At least two 1 ml samples of each concentration are used. Each 1 ml sample is evaluated by incubating as described above. The average number of colonies is given.

TABLE VII

| Product | Dose | T = 0 hrs | 1 hr | 7 hr | 14 hr | 26 hr |
|---|---|---|---|---|---|---|
| Blank | — | 140 M | 172 M | 155 M | 137 M | 137 M |
| CW-1720 | 100 ppm | | 13 M | 5 M | 4 M | 25 M |
| | 200 ppm | | 325 K | 20 K | 45 K | 13 M |
| | 300 ppm | | 60 K | 10 K | 15 K | 12 M |
| 20% Dispersion | 100 ppm | | 4 M | 4 M | 4 M | 20 M |
| | 200 ppm | | 80 K | 15 K | 35 K | 11 M |
| | 300 ppm | | 15 K | 10 K | 35 K | 22 M |
| satd. NaCl | 100 ppm | | 5 M | 25 M | 35 M | 50 M |
| | 300 ppm | | 22 M | 20 M | 42 M | 52 M |
| | 600 ppm | | 8 M | 17 M | 22 M | 57 M |

K=10,000 counts (10 thousand); M=1,000,000 counts (1 million) CW-1720=20% DBNPA solution in PEG 200 (from Dow Chemical) and water 20% Dispersion=20% DBNPA in viscosified brine solution—example (A) above It is evident from the above data that the untreated water sample (blank) had excessively high numbers of colonies, difficult to quantify accurately; and that in each sample of treated water, the biocidal effect of the DBNPA is greatest within the first 14 hr.

At 100 ppm each, DBNPA in 20% PEG solution fails to meet the criterion of "effective amount"; the effect of 20% DBNPA in viscosified brine is about three times more effective than the 20% solution in PEG after 1 hour; and its biocidal effectiveness decreases rapidly so as to be about the same as that of the 20% PEG solution after 7 hr, 14 hr and 26 hr.

At 200 ppm each, the effect of 20% DBNPA in viscosified brine is about four times more effective than the 20% solution in PEG after 1 hour; its biocidal effectiveness is about the same after 7 hr, 14 hr and 26 hr. As desired, the effectiveness of each is lost after 26 hr.

At 300 ppm each, the effect of 20% DBNPA in viscosified brine is again about four times more effective than the 20% solution in PEG after 1 hour; its biocidal effectiveness is about the same after 7 hr; after 14 hr and 26 hr, it is seen that the effectiveness of the DBNPA in dispersion has been dissipated more quickly than that of the DBNPA in solution, the number of colonies being twice as great on the plate smeared with the DBNPA in PEG solution.

The effect of NaCl used as brine has a discernible but slight biocidal effect, and there is no reason to believe that equivalent concentrations of any other water soluble alkali metal halide, NaBr is particular, or alkaline earth metal halide, $CaCl_2$ in particular, would have a substantially different effect.

Having thus provided a general discussion, described the overall process in detail and illustrated the invention with specific illustrations of the best mode of making and using it, it will be evident that using the dispersion of DBNPA avoids using a polyalkylene glycol yet is stable in storage and highly effective when diluted for use as a biocide. It is therefore to be understood that no undue restrictions are to be imposed by reason of the specific embodiments illustrated and discussed, and particularly that the invention is not restricted to a slavish adherence to the details set forth herein.

We claim:

1. A physically and chemically stable, saline dispersion of 2,2-dibromo-3-nitrilopropionamide (DBNPA) particles present in a concentration in the range from about 20 parts to 50 parts by weight of DBNPA per 100 parts of dispersion, in a restrictedly viscosified liquid brine solution having a viscosity in the range from about 340 cP (Brookfield #2 spindle, 30 rpm) to 30,000 cP (Brookfield #4 spindle, 6 rpm) at 25° C.;

the brine having dissolved therein a halide selected from the group consisting of an alkali metal halide, an alkaline earth metal halide, and a combination of one with another, in an amount at least 20% by weight of the amount required to saturate 100 parts of water;

the brine solution being viscosified with at least one viscosifier unreactive with the DBNPA;

the viscosifier being present in a concentration in the range from about 0.3% but less than 1% by weight of the dispersion, insufficient to gel the dispersion, physical stability of which dispersion, at the concentration of viscosifier, decreases as concentration of DBNPA at the concentration increases;

wherein less than 3% by weight of DBNPA in a 20% DBNPA dispersion is hydrolyzed upon being stored in a closed container for 3 weeks at a temperature in the range from about −5° C. to 35° C., and less than 3% by weight of DBNPA in the dispersion settles as solid particles in the container upon being stored during the same period and under the same conditions.

2. The dispersion of claim 1 wherein the halide is selected from the group consisting of sodium bromide, sodium chloride, calcium bromide and calcium chloride.

3. The dispersion of claim 2 wherein the brine solution consists essentially of a major portion by weight of sodium bromide and a minor proportion by weight of sodium chloride relative to the total amount of halides in solution, and the viscosifier is present in an amount in the range from about 0.3 to 0.8% by weight of the dispersion; and the pH of the brine prior to addition of the DBNPA is in the range from above 4 but less than 6.

4. The dispersion of claim 2 wherein a viscosifier is selected from a hydrophilic gum present in an amount in the range from 0.1% to 0.7% by wt, and a suspension aid in an amount in the range from 0.05% to 0.2% by wt of the dispersion, and a combination of one with the other.

5. The dispersion of claim 4 wherein the hydrophilic gum is a water-soluble polysaccharide in an amount in the range from about 0.4% to 0.6% by weight of the dispersion, wherein less than 3% by weight of DBNPA in the dispersion is hydrolyzed upon being stored in a closed container for 3 months at a temperature in the range from about −5° C. to 25° C., and less than 3% by weight of DBNPA in the dispersion settles as solid particles in the container upon being stored during the same period and under the same conditions.

6. The dispersion of claim 4 wherein the brine solution is essentially saturated with respect to at least one halide.

7. The dispersion of claim 6 wherein the brine solution contains a combination of sodium bromide and sodium chloride present in the range from 40 to 80 parts per 100 parts of water.

* * * * *